United States Patent
Gerke et al.

(10) Patent No.: US 9,458,081 B2
(45) Date of Patent: *Oct. 4, 2016

(54) PHOTOLABILE PRO-FRAGRANCES

(71) Applicant: Henkel AG & Co. KGaA, Duesseldorf (DE)

(72) Inventors: Thomas Gerke, Duesseldorf (DE); Christian Kropf, Hilden (DE); Ursula Huchel, Cologne (DE); Axel Griesbeck, Cologne (DE); Agnieszka Landes, Bergheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,977

(22) Filed: Dec. 15, 2014

(65) Prior Publication Data

US 2015/0099809 A1    Apr. 9, 2015

Related U.S. Application Data

(63) Continuation of application No. PCT/EP2013/058681, filed on Apr. 26, 2013.

(30) Foreign Application Priority Data

Jun. 22, 2012  (DE) .................. 10 2012 210 567
Sep. 5, 2012  (DE) .................. 10 2012 215 693

(51) Int. Cl.

| | |
|---|---|
| *C07C 59/84* | (2006.01) |
| *C07C 69/738* | (2006.01) |
| *A61K 8/37* | (2006.01) |
| *A61K 8/365* | (2006.01) |
| *A61Q 13/00* | (2006.01) |
| *C07C 59/90* | (2006.01) |
| *C11B 9/00* | (2006.01) |
| *C11D 3/50* | (2006.01) |
| *A61Q 19/00* | (2006.01) |

(52) U.S. Cl.
CPC ............... *C07C 59/84* (2013.01); *A61K 8/365* (2013.01); *A61K 8/37* (2013.01); *A61K 8/375* (2013.01); *A61Q 13/00* (2013.01); *A61Q 19/00* (2013.01); *C07C 59/90* (2013.01); *C07C 69/738* (2013.01); *C11B 9/0061* (2013.01); *C11D 3/50* (2013.01); *C11D 3/507* (2013.01); *A61K 2800/57* (2013.01)

(58) Field of Classification Search
None
See application file for complete search history.

(56) References Cited

U.S. PATENT DOCUMENTS

| | | | | |
|---|---|---|---|---|
| 8,129,569 | B2 * | 3/2012 | Huchel | ................... A61K 8/31 424/70.1 |
| 8,466,294 | B2 | 6/2013 | Huchel et al. | |
| 8,604,250 | B2 | 12/2013 | Gerke et al. | |

FOREIGN PATENT DOCUMENTS

| | | |
|---|---|---|
| WO | 2004/045616 A1 | 6/2004 |
| WO | 2004/099132 A2 | 11/2004 |

OTHER PUBLICATIONS

Levrand et al. Photochem. Photobiol., Sci (2002): 1, 907-919.*
Nerurkar et al. (β-Arylgutaconic acids (1960); 25; 1491-1495.*
PCT International Search Report (PCT/EP2013/058681) dated Jun. 24, 2013.
Basu et al., "KF—Alumina-Mediated Selective Double Michael Additions of Aryl Methyl Ketones: A Facile Entry to the Synthesis of Functionalized Pimelate Esters and Derivatives", XP-002649372, Synlett, No. 12, pp. 2224-2226, 2004.
Mulzer et al., "Additionen von Carbonsaure-Dianionen an α, β-ungesattigte Carbonylverbindungen Steuerung der I,2-/1,4-Regioselektivitat durch sterische Substituenteneffekte", XP-055064770, Chemische Berichte, vol. 114, No. 11, pp. 3701-3724, 1981.
Kohler et al., "Studies in the Cyclopropane Series. IV.", XP-055064771, Journal of the American Chemical Society, vol. 41, No. 6, pp. 992-1001, 1919.
Onishi et al., "InCI3/Me3 SiBr-Catalyzed Direct Coupling between Silyl Ethers and Enol Acetates", XP-055064872, Organic Letters, vol. 13, No. 10, pp. 2762-2765, 2011.
Shintani et al. "Highly Enantioselective Desymmetrization of Anhydrides by Carbon Nucleophiles: Reactions of Grignard Reagents in the Presence of (—)-Sparteine", XP-002698014, Angew. Chem. Int. Ed., vol. 41, No. 6, pp. 1057-1059, 2002.
Ghatge et al., "Preparation of β-aryl, γ-aroyl Butyric Acids: the Attempted Synthesis of Hydantoin Analogues", XP-008162603, J. Indian Chem. Soc., vol. 58, pp. 90-91, 1981.
Murphy et al., "Reductive Cleavage of Arylcyclopropyl Ketones" XP-002698015, J. Chem. Soc. Perkin Trans. 1, pp. 1445-1451, 1986.
Shin et al., "Effect of the Alkyl Chain Length of C70-PCBX Acceptors on the Device Performance of P3HT : C70-PCBX Polymer Solar Cells", XP-002698066, Journal of Materials Chemistry, vol. 21, pp. 960-967, 2011.

\* cited by examiner

*Primary Examiner* — Shirley V Gembeh
(74) *Attorney, Agent, or Firm* — Thomas G. Krivulka

(57) ABSTRACT

Many fragrances that provide a scent of freshness tend to be highly volatile and are therefore not very economical when used in typical applications such as washing or cleaning processes, so they have to be used in relatively large quantities to be able to produce adequate effects. The disclosed photolabile pro-fragrances provide a much longer-lasting sense of fragrance, in particular with a scent of freshness, when used in typical applications, thus allowing said fragrances to be used efficiently.

11 Claims, No Drawings

PHOTOLABILE PRO-FRAGRANCES

FIELD OF THE INVENTION

The present invention generally relates to special compounds that function as photolabile pro-fragrances for scent acids and scent esters. The present invention further relates to washing or cleaning agents, cosmetic agents, and room scenting agents that contain such compounds. It further relates to a method for long-lasting scenting of surfaces, and likewise to a method for long-lasting room scenting.

BACKGROUND OF THE INVENTION

Washing or cleaning agents, or cosmetic agents, usually contain scents that impart a pleasant odor to the agents. The scents also mask any odor of the other ingredients, so that the consumer receives a pleasant olfactory impression.

In the washing-agent sector in particular, scents are important constituents of the composition, since the laundry is intended to have a pleasant and, if possible, also fresh scent in both the wet and the dry state. A fundamental problem encountered when using scents is that they are more or less volatile compounds, but that a long-lasting scent effect is nevertheless desirable. The desired longevity of the scent impression is very difficult to achieve in particular with those fragrances which represent the fresh and light notes of the perfume and volatilize particularly quickly because of their high vapor pressure.

Delayed scent release can occur, for example, thanks to the carrier-bound use of scents. A carrier-bound precursor form of a scent is also referred to as a "pro-fragrance." In this connection, international patent application WO 2007/087977 discloses the use of 1-aza-3,7-dioxabicyclo[3.3.0]octane compounds as pro-fragrances for delayed release of scent aldehydes and scent ketones by hydrolysis. An alternative possibility for delayed release of scents is represented by the use of so-called photoactivatable substances as pro-fragrances. Breakage of a covalent bond in the pro-fragrance molecule is induced by the action of sunlight or another electromagnetic radiation source of a specific wavelength, with the result that a scent is released.

WO 2011/101180 discloses the use of specific ketones as photoactivatable substances which, in the presence of light, release an active agent in a photochemical fragmentation. The aforesaid active agent possesses, for example a scenting activity that is released only in delayed fashion, and over a long time period, on a specific surface as a result of the photochemically induced breakdown. Hitherto, however, only the release of scent ketones is known. The delayed release of scents other than ketones is important, however, so that as broad a spectrum as possible of long-lasting scent impressions can be furnished to the consumer.

The object of the present invention is to furnish photoactivatable substances, constituting pro-fragrances, that permit delayed release of scent esters, in particular of cinnamic acid esters and derivatives of cinnamic acid esters.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A compound of the general formula (I)

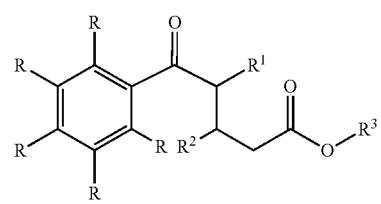

formula (I)

wherein R1 denotes hydrogen, a linear or branched, substituted or unsubstituted alkyl, aryl, or alkenyl group; R2 and R3 mutually independently denote hydrogen, a linear or branched, substituted or unsubstituted alkyl, aryl, or alkenyl group; and each R mutually independently denotes hydrogen, an amino group, $-NO_2$, a linear or branched, substituted or unsubstituted alkoxy group having 1 to 15 carbon atoms, a linear or branched, substituted or unsubstituted alkyl group having 1 to 15 carbon atoms, a cycloalkyl group, acyl group, aryl group, $-OH$, $-NH_2$, halogen, NH-alkyl, or $-N(alkyl)_2$.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention achieved by a compound of the general formula (I),

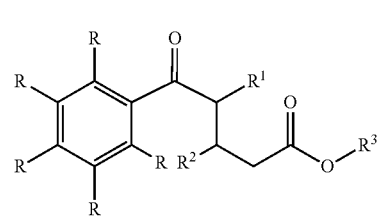

formula (I)

wherein
R1 denotes hydrogen, a linear or branched, substituted or unsubstituted alkyl, aryl, or alkenyl group,
R2 and R3 mutually independently denote hydrogen, a linear or branched, substituted or unsubstituted alkyl, aryl, or alkenyl group, and
each R mutually independently denotes hydrogen, an amino group, $-NO_2$, a linear or branched, substituted or unsubstituted alkoxy group having 1 to 15 carbon atoms, a linear or branched, substituted or unsubstituted alkyl group having 1 to 15 carbon atoms, a cycloalkyl group, acyl group, aryl group, $-OH$, $-NH_2$, halogen, NH-alkyl, or $-N(alkyl)_2$.

It has been found, surprisingly, that the compounds according to the present invention of the general formula (I) are particularly effective pro-fragrances that permit delayed release of scent acids and scent esters, in particular of scent esters, and in particular of cinnamic acid esters and derivatives of cinnamic acid esters. Utilization of the compounds according to the present invention in washing or cleaning agents, cosmetic agents, or room scenting agents results, when they are utilized, in an improved long-term scent effect, in particular in connection with textile treatment. In the context of utilization of compounds according to the present invention in a laundry treatment agent, such as a washing agent and conditioner, an improved long-term scenting effect on the treated laundry was thus encountered. In addition, corresponding products exhibit particularly good shelf stability. The agents according to the present invention furthermore make it possible to reduce the total quantity of perfume that is contained in the agent, and nevertheless to achieve odor advantages on the washed textiles, in particular with regard to a perception of freshness.

A preferred embodiment of the present invention relates in particular to pro-fragrances of scent esters.

The compound according to the present invention in accordance with the general formula (I) is suitable as a pro-fragrance for all usual scent esters that, in their free form, comprise as a scent an alpha,beta-unsaturated carbonyl unit, or mesomeric boundary forms thereof. Preferred scent esters are selected from cinnamic acid esters and derivatives of cinnamic acid esters. Linaloyl cinnamate, 3-phenylpropyl cinnamate, eugenol cinnamate, allyl cinnamate, benzyl cinnamate, butyl cinnamate, ethyl cinnamate, methyl cinnamate, menthyl cinnamate, heptyl cinnamate, cyclohexyl cinnamate, isoamyl cinnamate, isobutyl cinnamate, isopentyl cinnamate, isopropyl cinnamate, isoheptyl cinnamate, tetrahydrofuryl cinnamate, and cinnamyl cinnamate are particularly preferred. The stored esters can be released by the action of light comprising the wavelengths from 200 to 400 nm.

According to a preferred embodiment of the invention, the substituent R2 in formula (I) denotes a substituted or unsubstituted aryl group, in particular a substituted or unsubstituted phenyl, particularly preferably an unsubstituted phenyl.

According to a further preferred embodiment of the invention, the substituent R1 in formula (I) denotes a linear or branched, substituted or unsubstituted alkyl group having 1 to 6 carbon atoms, preferably 1 to 3 carbon atoms, in particular is a methyl residue.

According to a further preferred embodiment of the invention, the substituent R3 in formula (I) denotes hydrogen, a methyl, ethyl, n-pentyl, sec-pentyl, cinnamyl, or citronellyl group.

According to a further preferred embodiment of the invention, a compound according to the present invention of the general formula (I) in which all substituents R denote hydrogen is preferred. In a further preferred embodiment of the invention, a compound according to the present invention of the general formula (I) in which four of the five aryl substituents R denote hydrogen is preferred. Preferably the four residues R in the ortho- and meta-positions of the aromatic denote hydrogen, while the residue in the para-position of the aromatic denotes a halogen atom, in particular —F, —Cl, or —Br, —NO₂, a linear or branched, substituted or unsubstituted alkoxy group having 1 to 6 carbon atoms, or a linear or branched, substituted or unsubstituted alkyl group having 1 to 6 carbon atoms. In a further preferred embodiment of the invention, the residue R in the para-position of the aromatic in formula (I) denotes —Cl, —Br, —NO₂, or an alkyl or alkoxy group having 1 to 4 carbon atoms. The residue R in the para-position of the aromatic is preferably a methyl or ethyl group or a methoxy, ethoxy, isopropoxy, or tert-butoxy group. A substitution in the para-position is particularly preferred, since the electron structure of the aromatic ring can be most effectively modified there, with the result that the absorption maximum of compounds of the general formula (I) can easily be adapted to a specific wavelength.

It is very particularly preferred if, in formula (I), one of the two residues R in the meta-position of the aromatic denotes an alkoxy group, in particular a methoxy group, and the residue R in the para-position of the aromatic denotes an alkoxy group, in particular a methoxy group, and the other residue R in the meta-position of the aromatic, like the two residues R in the ortho-position of the aromatic, denote hydrogen.

According to a preferred embodiment of the invention, compounds of formula (I) correspond to one of the following formulas (II) to (ILIV)

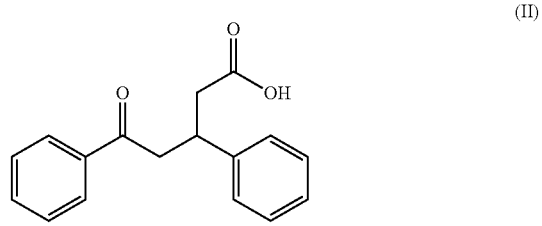

(II)

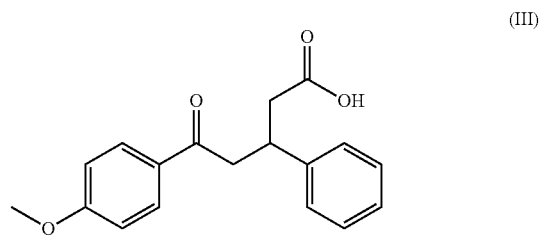

(III)

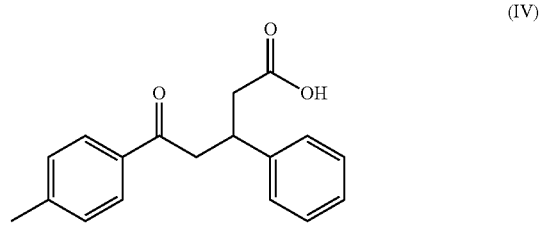

(IV)

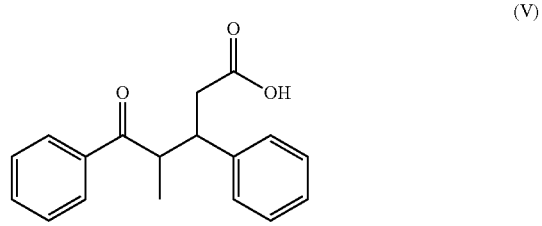

(V)

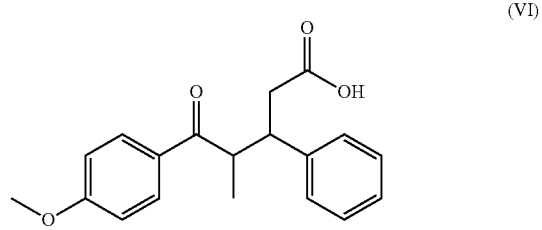

(VI)

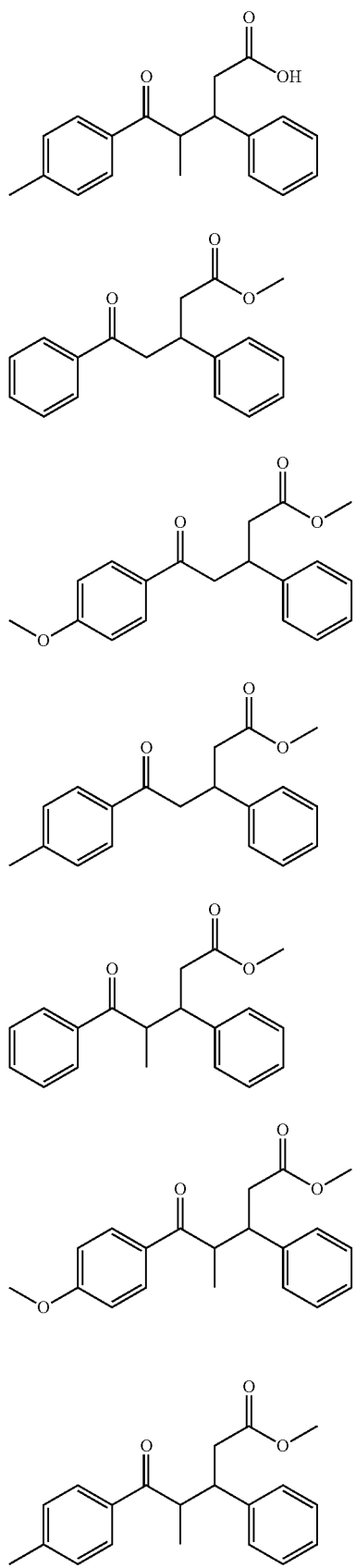
(VII)
(VIII)
(IX)
(X)
(XI)
(XII)
(XIII)
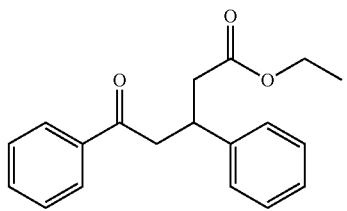
(XIV)
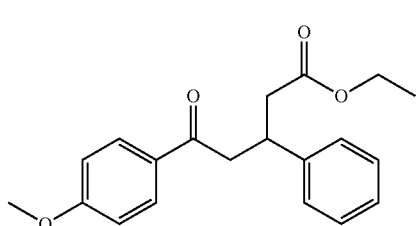
(XV)
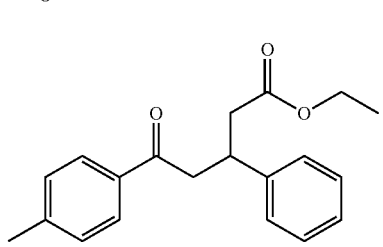
(XVI)
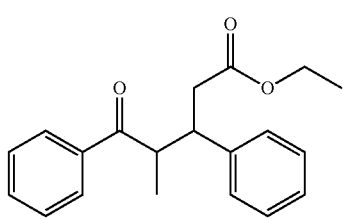
(XVII)
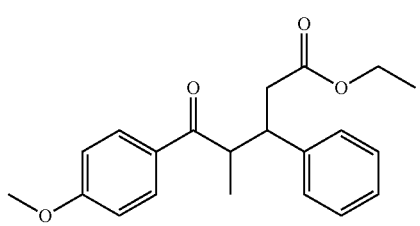
(XVIII)
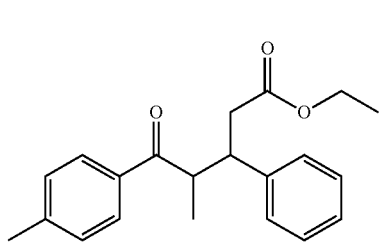
(XIX)
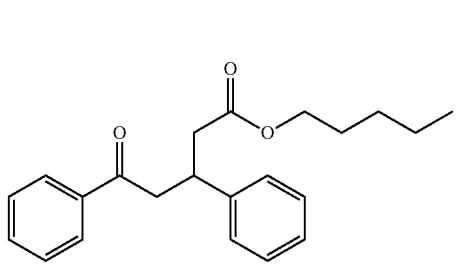
(XX)

-continued
(XXI)
(XXII)
(XXIII)
(XXIV)
(XXV)
(XXVI)
(XXVII)
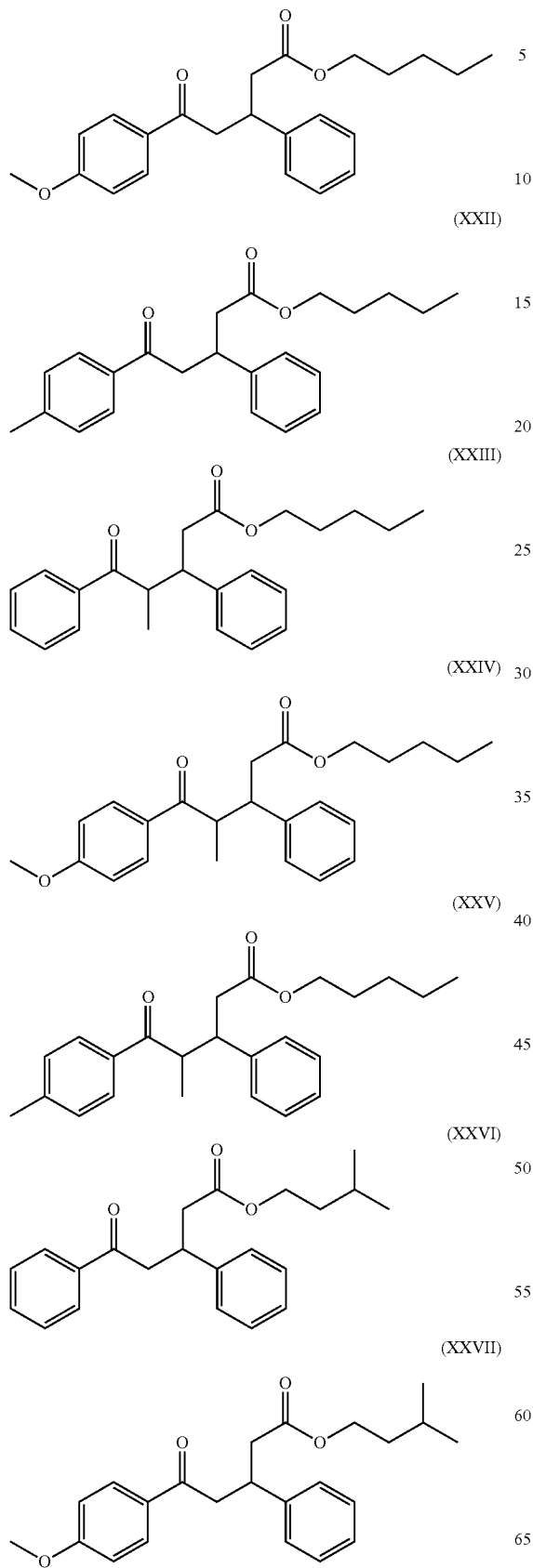
-continued
(XXVIII)
(XXIX)
(XXX)
(XXXI)
(XXXII)
(XXXIII)
(XXXIV)
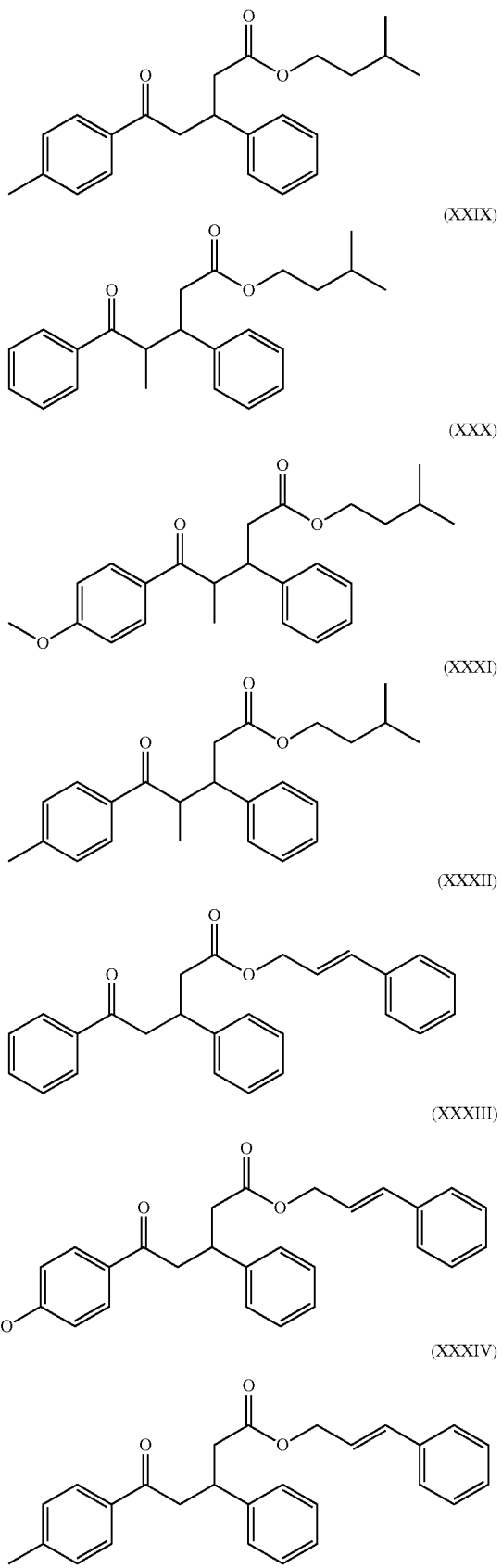

(XXXV)
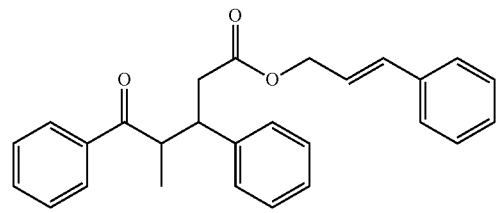

(XXXVI)
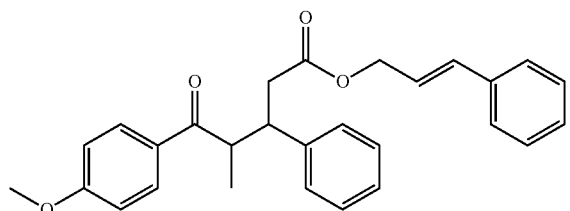

(XXXVII)
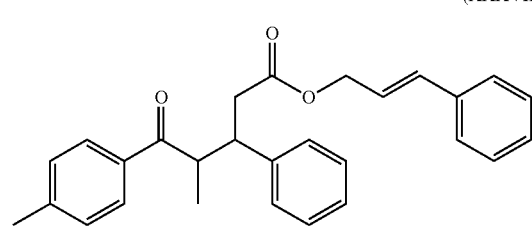

(XXXVIII)
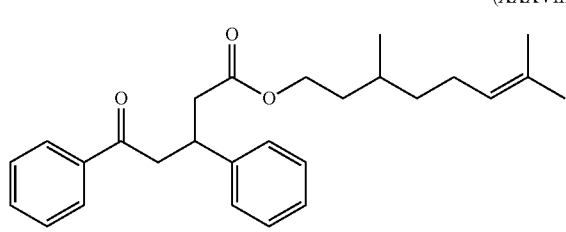

(XXXIX)
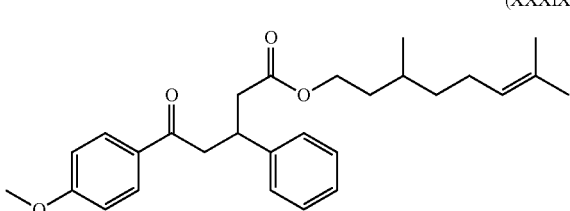

(IL)
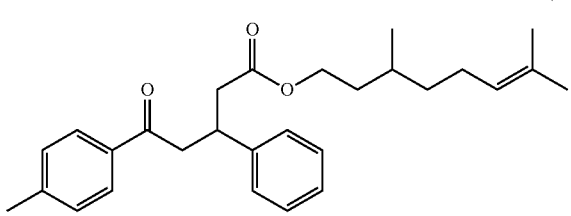

(ILI)
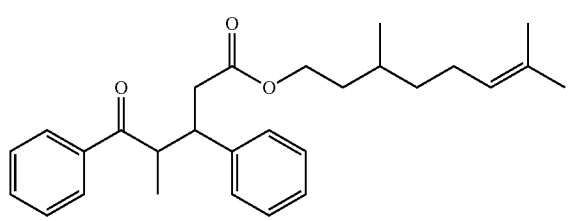

(ILII)
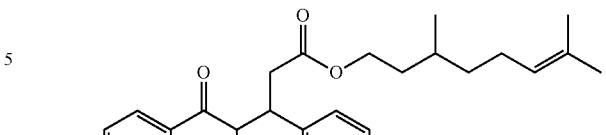

(ILIII)
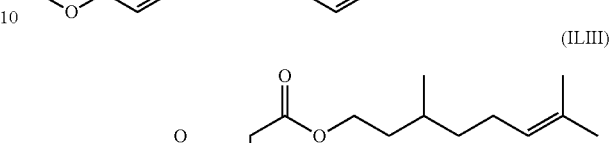

(ILIV)
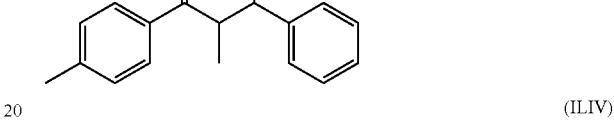

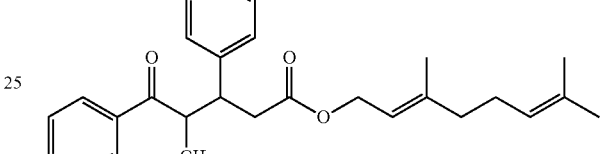

Compounds according to formula (I), in particular the compounds of the aforesaid formulas (II) to (ILIV), can be incorporated in stable fashion into the usual washing- or cleaning-agent matrices, into cosmetics, and into existing fragrance compositions. They enable delayed release of the stored scents, namely of cinnamic acid esters or derivatives of cinnamic acid esters. These compounds impart a particularly long-lasting fresh impression to usual washing or cleaning agents and to cosmetics. The dried, washed textile profits in particular from the good long-term fresh impression. Slow release of the stored fragrance occurs after the action of light (electromagnetic radiation) comprising the wavelengths from 200 to 400 nm, as illustrated in simplified fashion in the reaction equation below:

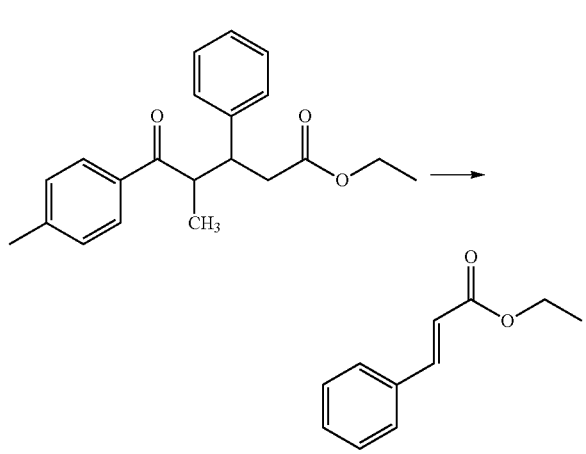

The use of compounds of formula (I) that have been modified by the introduction of special substituents R, preferably methyl or methoxy, results in light absorption in a higher wavelength range. Upon exposure of these compounds to natural light or to light that is generated by ordinary household illumination devices, fragrance quantities above the odor threshold are released particularly quickly, thereby increasing the effectiveness of the compounds of formula (I).

A further subject of the present invention is a washing or cleaning agent, preferably a washing agent, conditioner, or washing adjuvant, containing at least one compound in accordance with one of formulas (I) to (ILIV), wherein the aforesaid compound is contained preferably in quantities between 0.0001 and 5 wt %, advantageously between 0.001 and 4 wt %, more advantageously between 0.01 and 3 wt %, in particular between 0.05 and 2 wt %, based in each case on the on the total agent. Suitable cleaning agents are, for example, cleaning agents for hard surfaces, such as preferably dishwashing agents. They can also be cleaning agents such as household cleaners, all-purpose cleaners, window cleaners, floor cleaners, etc. The product can preferably be one for cleaning toilet bowls and urinals, advantageously a flush cleaner for suspension in the toilet bowl, in particular a so-called toilet block.

According to a preferred embodiment of the invention, the washing or cleaning agent according to the present invention contains at least one surfactant selected from anionic, cationic, nonionic, zwitterionic, amphoteric surfactants, or mixtures thereof.

According to a further preferred embodiment of the invention, the agent according to the present invention is present in solid or liquid form.

A further subject of the invention is a cosmetic agent containing at least one compound in accordance with one of formulas (I) to (ILIV), which agent contains the aforesaid compound preferably in quantities between 0.0001 and 5 wt %, advantageously between 0.001 and 4 wt %, more advantageously between 0.01 and 3 wt %, in particular between 0.05 and 2 wt %, based in each case on the total agent.

A further subject of the invention is a room scenting agent (e.g. room air freshener, room deodorant, room spray, etc.) containing at least one compound in accordance with one of formulas (I) to (ILIV), wherein said compound is contained preferably in quantities between 0.0001 and 50 wt %, advantageously between 0.001 and 5 wt %, more advantageously between 0.1 and 3 wt %, in particular between 0.1 and 2 wt %, based in each case on the total agent.

According to a further preferred embodiment of the invention, additional scents, selected in particular from the group comprising scents of natural or synthetic origin, preferably more-volatile scents, higher-boiling scents, solid scents, and/or adherent scents, are contained in an agent according to the present invention (e.g. washing or cleaning agent, cosmetic agent, or room scenting agent).

Adherent scents that are usable with advantage in the context of the present invention are, for example, essential oils such as angelica oil, anise oil, arnica flower oil, basil oil, bay oil, bergamot oil, champaca flower oil, silver fir oil, silver fir cone oil, elemi oil, eucalyptus oil, fennel oil, fir needle oil, galbanum oil, geranium oil, gingergrass oil, guaiac wood oil, balsam guijun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, spearmint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, orange oil, oregano oil, palmarosa oil, patchouli oil, balsam peru oil, petitgrain oil, pepper oil, peppermint oil, pimento oil, pine oil, rose oil, rosemary oil, sandalwood oil, celery oil, spilt oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citron oil, and cypress oil.

Higher-boiling or solid fragrances of natural or synthetic origin can, however, also be used in the context of the present invention as adherent scents or scent mixtures. Included among these compounds are the compounds recited below as well as mixtures thereof: ambrettolide, alpha-amylcinnamaldehyde, anethole, anisaldehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, bomeol, bornyl acetate, alpha-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl beta-naphthyl ketone, methyl-n-nonylacetaldehyde, methyl n-nonyl ketone, muscone, beta-naphthol ethyl ether, beta-naphthol methyl ether, nerol, nitrobenzene, n-nonylaldehyde, nonyl alcohol, n-octylaldehyde, p-oxyacetophenone, pentadecanolide, beta-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undelactone, vanillin, veratrumaldehyde, cinnamaldehyde, cinnamyl alcohol, cinnamic acid, cinnamic acid ethyl ester, cinnamic acid benzyl ester.

Included among the more-volatile scents are, in particular, the lower-boiling scents of natural or synthetic origin, which can be used alone or in mixtures. Examples of more-volatile scents are alkyl isothiocyanates (alkyl mustard oils), butanedione, limonene, linalool, linalyl acetate and linalyl propionate, menthol, menthone, methyl-n-heptenone, phellandrene, phenylacetaldehyde, terpinyl acetate, citral, citronellal.

According to a further preferred embodiment, the agent according to the present invention, i.e. washing or cleaning agent, cosmetic agent, or room scenting agent, comprises at least one, preferably multiple, active components, in particular components having washing, care-providing, or cleaning activity and/or cosmetic components, advantageously selected from the group comprising anionic surfactants, cationic surfactants, amphoteric surfactants, nonionic surfactants, alkalizing agents, anti-creasing compounds, antibacterial substances, antioxidants, anti-redeposition agents, antistatic agents, builder substances, bleaching agents, bleach activators, bleach stabilizers, bleach catalysts, ironing adjuvants, co-builders, scents, shrinkage preventers, electrolytes, enzymes, color protectants, coloring agents, dyes, color transfer inhibitors, fungicides, germicides, odor-complexing substances, adjuvants, hydrotropes, rinse aids, complexing agents, preservatives, corrosion inhibitors, water-miscible organic solvents, optical brighteners, perfumes, perfume carriers, luster agents, pH adjusting agents, proofing and impregnation agents, polymers, swelling and anti-slip agents, foam inhibitors, sheet silicates, dirt-repelling substances, silver protectants, silicone oils, soil release active substances, UV protection substances, viscosity regulators, thickening agents, vitamins, and/or softening compounds. For purposes of this invention, indications for the agent according to the present invention in wt % refer, unless otherwise indicated, to the total weight of the agent according to the present invention.

The quantities of the individual ingredients in the agents according to the present invention, i.e. washing or cleaning agents, cosmetic agents, or room scenting agents, are aimed in each case toward the intended use of the relevant agent, and the skilled artisan is familiar in principle with the orders of magnitude of the quantities of ingredients to be used or can gather them from the relevant technical literature. The surfactant content, for example, will be selected to be higher or lower depending on the intended use of the agents according to the present invention.

The agents according to the present invention (i.e. washing or cleaning agents, cosmetic agents, or room scenting agents) can contain surfactants, wherein anionic surfactants, nonionic surfactants, and mixtures thereof, but also cationic surfactants, are preferably suitable.

Surfactants are contained as applicable in the agents according to the present invention, i.e. washing or cleaning agents, cosmetic agents, or room scenting agents, in quantitative proportions preferably from 5 wt % to 50 wt %, in particular from 8 wt % to 30 wt %. In laundry post-treatment agents in particular, preferably up to 30 wt %, in particular 5 wt % to 15 wt % surfactants, among them preferably cationic surfactants at least in part, are employed.

Suitable nonionic surfactants are in particular ethoxylation and/or propoxylation products of alkyl glycosides and/or of linear or branched alcohols each having 12 to 18 carbon atoms in the alkyl portion and 3 to 20, preferably 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 carbon atoms in the alkyl residue.

Suitable anionic surfactants are, in particular, soaps, and those which contain sulfate or sulfonate groups having preferably alkali ions as cations. Usable soaps are preferably the alkali salts of saturated or unsaturated fatty acids having 12 to 18 carbon atoms. Such fatty acids can also be used in incompletely neutralized form. Included among the usable surfactants of the sulfate type are salts of sulfuric acid semiesters of fatty alcohols having 12 to 18 carbon atoms, and sulfatization products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants are preferably selected from esterquats and/or quaternary ammonium compounds (QACs) in accordance with the general formula $(R^I)(R^{II})(R^{III})(R^{IV})N^+ X^-$, in which $R^I$ to $R^{IV}$ denote identical or different $C_{1-22}$ alkyl residues, $C_{7-28}$ aralkyl residues, or heterocyclic residues, wherein two (or in the case of an aromatic bond such as in pyridine, even three) residues form, together with the nitrogen atom, the heterocycle (e.g. a pyridinium or imidazolinium compound), and denotes halide ions, sulfate ions, hydroxide ions, or similar anions. QACs can be manufactured by the reaction of tertiary amines with alkylating agents such as methyl chloride, benzyl chloride, dimethyl sulfate, dodecyl bromide, but also ethylene oxide. The alkylation of tertiary amines having a long alkyl residue and two methyl groups can be achieved particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-$C_{1-2}$ alkylammonium chloride), benzoxonium chloride (benzyldodecyl-bis(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are benzalkonium chlorides having $C_8$ to $C_{22}$ alkyl residues, in particular $C_{12}$ to $C_{14}$ alkylbenzyldimethylammonium chloride.

Preferred esterquats are methyl-N-(2-hydroxyethyl)-N,N-di(tallowacyloxyethyl)ammonium metho sulfate, bis(palmitoyl)ethylhydroxyethylmethylammonium metho sulfate, or methyl-N,N-bis(acyloxyethyl)-N-(2-hydroxyethyl)ammonium methosulfate. Commercially usual examples are the methylhydroxyalkyldialkoyloxyalkylammonium methosulfates marketed by the Stepan Company under the Stepantex® trademark, or the products of BASF SE known under the trade name Dehyquart® or the products of the manufacturer Evonik Industries AG known under the name Rewoquat®.

An agent according to the present invention, in particular a washing or cleaning agent, preferably contains at least one water-soluble and/or water-insoluble, organic and/or inorganic builder. Included among the water-soluble organic builder substances are polycarboxylic acids, in particular citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminete trakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain, polymerized into them, small proportions of polymerizable substances having no carboxylic-acid functionality.

Suitable (although less preferred) compounds of this class are copolymers of acrylic acid or methacrylic acid with vinyl ethers, such as vinyl methyl ethers, vinyl esters, ethylene, propylene, and styrene, in which the proportion of acid is equal to at least 50 wt %. All the aforesaid acids are used as a rule in the form of water-soluble salts thereof, in particular alkali salts thereof.

Organic builder substances can be contained, if desired, in quantities of up to 40 wt %, in particular up to 25 wt %, and preferably from 1 to 8 wt %. Quantities close to the aforesaid upper limit are used preferably in pasty or liquid, in particular water-containing, agents according to the present invention. Laundry post-treatment agents according to the present invention, for example fabric softeners, can also optionally be free of organic builder.

Possibilities as water-soluble inorganic builder materials are, in particular, alkali silicates and polyphosphates, preferably sodium triphosphate, for example zeolite A, P, or X.

Inorganic builder substances are contained, if desired, in the agents according to the present invention preferably in quantities of up to 60 wt %, in particular from 5 to 40 wt %. Laundry post-treatment agents according to the present invention, for example fabric softeners, are preferably free of inorganic builder.

Peroxygen compounds that are suitable are, in particular, organic peracids or peracidic salts of organic acids such as phthalimidopercaproic acid, perbenzoic acid, or salts of diperdodecanedioic acid, hydrogen peroxide, and inorganic salts that release hydrogen peroxide under utilization conditions, such as perborate, percarbonate, and/or persilicate. The addition of small quantities of known bleaching-agent stabilizers, for example phosphonates, borates or metaborates, and metasilicates, as well as magnesium salts such as magnesium sulfate, can be useful.

Suitable enzymes usable in the agents are those from the class of proteases, cutinases, amylases, pullulanases, hemicellulases, cellulases, lipases, oxidases, and peroxidases, as well as mixtures thereof. Enzymatic active substances recovered from fungi or bacteria, such as *Bacillus subtilis, Bacillus licheniformis, Streptomyces griseus, Humicola lanuginosa, Humicola insolens, Pseudomonas pseudoalcaligenes,* or *Pseudomonas cepacia,* are particularly suitable. The enzymes that are optionally used can be adsorbed onto carrier substances and/or embedded into encasing substances in order to protect them from premature inactivation. They are contained, if desired, in the agents according to the present invention preferably in quantities not above 5 wt %, in particular from 0.2 to 2 wt %.

Production of the compounds according to the present invention is described by way of example in the Examples section, with reference to the manufacture of a pro-fragrance that contains a cinnamic acid ester. Other compounds of the general formula (I), and in particular all compounds of formula (II) to (ILIV), are also accessible by this basic synthesis route.

According to a preferred embodiment, the teaching of the present invention can be employed to significantly decrease the proportion of perfume in washing or cleaning agents and cosmetic agents. As a result, it is possible to offer perfumed products even for those particularly sensitive consumers who, because of specific incompatibilities and irritations, can use normally perfumed products only to a limited extent or not at all.

A preferred solid, in particular powdered, washing agent according to the present invention can also in particular contain, besides the compound according to the present invention, components that are selected, for example, from the following:
    anionic surfactants such as preferably alkylbenzenesulfonate, alkyl sulfate, e.g. in quantities preferably from 5 to 30 wt %,
    nonionic surfactants such as preferably fatty alcohol polyglycol ethers, alkyl polyglucoside, fatty acid glucamide, e.g. in quantities preferably from 0.5 to 15 wt %, builders, for example zeolite, polycarboxylate, sodium citrate, in quantities e.g. from 0 to 70 wt %, advantageously 5 to 60 wt %, preferably 10 to 55 wt %, in particular 15 to 40 wt %,
    alkalis, for example sodium carbonate, in quantities e.g. from 0 to 35 wt %, advantageously 1 to 30 wt %, preferably 2 to 25 wt %, in particular 5 to 20 wt %,
    bleaching agents, for example sodium perborate, sodium percarbonate, in quantities e.g. from 0 to 30 wt %, advantageously 5 to 25 wt %, preferably 10 to 20 wt %,
    corrosion inhibitors, e.g. sodium silicate, in quantities e.g. from 0 to 10 wt %, advantageously 1 to 6 wt %, preferably 2 to 5 wt %, in particular 3 to 4 wt %,
    stabilizers, e.g. phosphonates, advantageously 0 to 1 wt %,
    foam inhibitor, e.g. soap, silicone oils, paraffins, advantageously 0 to 4 wt %, preferably 0.1 to 3 wt %, in particular 0.2 to 1 wt %,
    enzymes, e.g. proteases, amylases, cellulases, lipases, advantageously 0 to 2 wt %, preferably 0.2 to 1 wt %, in particular 0.3 to 0.8 wt %,
    anti-gray agent, e.g. carboxymethyl cellulose, advantageously 0 to 1 wt %,
    discoloration inhibitor, e.g. polyvinylpyrrolidone derivatives, preferably 0 to 2 wt %,
    adjusting agent, e.g. sodium sulfate, advantageously 0 to 20 wt %,
    optical brighteners, e.g. stilbene derivatives, biphenyl derivatives, advantageously 0 to 0.4 wt %, in particular 0.1 to 0.3 wt %,
    optionally further scents,
    optionally water,
    optionally soap,
    optionally bleach activators,
    optionally cellulose derivatives,
    optionally dirt repellents,
"wt %" being based in each case on the total agent.

In another preferred embodiment of the invention, the agent is present in liquid form, preferably in gel form. Preferred liquid washing or cleaning agents contain water as a principal solvent, and optionally non-aqueous solvents.

A preferred liquid, in particular gel-type, washing agent according to the present invention can in particular also contain, besides the compound according to the present invention, components that are selected e.g. from the following:
    anionic surfactants such as preferably alkylbenzenesulfonate, alkyl sulfate, e.g. in quantities preferably from 5 to 40 wt %,
    nonionic surfactants such as preferably fatty alcohol polyglycol ethers, alkyl polyglucoside, fatty acid glucamide, e.g. in quantities preferably from 0.5 to 25 wt %,
    builders, for example polycarboxylate, sodium citrate, advantageously 0 to 15 wt %, preferably 0.01 to 10 wt %, in particular 0.1 to 5 wt %,
    foam inhibitor, e.g. soap, silicone oils, paraffins, in quantities e.g. from 0 to 10 wt %, advantageously 0.1 to 4 wt %, preferably 0.2 to 2 wt %, in particular 1 to 3 wt %,
    enzymes, e.g. proteases, amylases, cellulases, lipases, in quantities e.g. from 0 to 3 wt %, advantageously 0.1 to 2 wt %, preferably 0.2 to 1 wt %, in particular 0.3 to 0.8 wt %,
    optical brightener, e.g. stilbene derivative, biphenyl derivative, in quantities e.g. from 0 to 1 wt %, advantageously 0.1 to 0.3 wt %, in particular 0.1 to 0.4 wt %,
    optionally further scents,
    optionally stabilizers,
    water, optionally soap, in quantities e.g. from 0 to 25 wt %, advantageously 1 to 20 wt %, preferably 2 to 15 wt %, in particular 5 to 10 wt %, optionally solvents (preferably alcohols), advantageously 0 to 25 wt %, preferably 1 to 20 wt %, in particular 2 to 15 wt %, "wt %" being based in each case on the total agent.

A preferred liquid fabric softener according to the present invention can in particular also contain, besides the compound according to the present invention, components that are selected from the following:

cationic surfactants, such as especially esterquats, e.g. in quantities from 2 to 30 wt %, co-surfactants, for example glycerol monostearate, stearic acid, fatty alcohols, fatty alcohol ethoxylates, e.g. in quantities from 0 to 5 wt %, preferably 0.1 to 4 wt %, emulsifier agents, for example fatty amine ethoxylates, e.g. in quantities from 0 to 4 wt %, preferably 0.1 to 3 wt %, optionally further scents, dyes, preferably in the ppm range, stabilizers, preferably in the ppm range, solvents, for example water, in quantities preferably from 60 to 90 wt %, "wt %" being based in each case on the total agent.

A further subject of the invention is a method for long-lasting scenting of surfaces, wherein a compound in accordance with one of formulas (I) to (ILIV) or a washing or cleaning agent according to the present invention is applied onto the surface to be scented (e.g. textile, dish, floor), and said surface is then exposed to an electromagnetic radiation comprising the wavelengths from 200 to 400 nm.

A further subject of the invention is a method for long-lasting room scenting, wherein a room scenting agent according to the present invention is exposed to an electromagnetic radiation comprising the wavelengths from 200 to 400 nm.

EXAMPLES

Example 1

Synthesis of Pro-Fragrances in Accordance with Formula (I)

Example 1a

Production of Methylchalcone (AB-15)

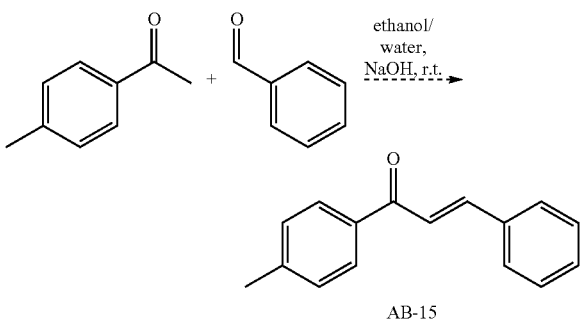

AB-15

4-Methylacetophenone was dissolved in an ethanol/water mixture; NaOH was added thereto, and benzaldehyde was slowly dripped in with ice-bath cooling. The reaction mixture was stirred overnight at room temperature. The reaction was extracted three times with $Et_2O$, washed with saturated NaCl solution, then dried over $MgSO_4$; solvent was removed under vacuum.

The resulting product was identified both via $^1$H-NMR spectroscopy and with GC/MS.

GC/MS: (50-300M), m/z: 222, 207, 180, 120, 92.

$t_R$ (50-300M)=14.276 min

M=268.31 g/mol

Example 1b

Production of 5-oxo-3,5-diphenylpentanoic acid (AB-01)

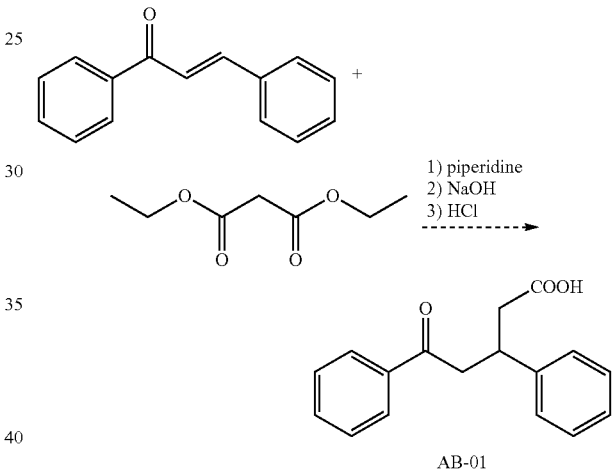

AB-01

A solution of chalcone, dimethyl malonate, and pyridine was heated in ethanol in a 100 ml round bottom flask with a reflux cooler, and stirred under reflux for 2 days.

After the reaction mixture had cooled, cold 4M caustic soda was dripped in, and the mixture was heated and stirred for 6 hours under reflux. The mixture was then cooled, cold concentrated hydrochloric acid was dripped in at room temperature to pH 1, and the reaction mixture was extracted three times with diethyl ether. The combined organic phases were washed with saturated NaCl solution, then dried over $MgSO_4$; the solvent was removed under vacuum.

M=268.31 g/mol

MP: 154-156° C.

$^1$H-NMR: (300 MHz, $C_2D_3N$)

δ (ppm)=8.03-7.07 (m, 10H); 3.81-3.70 (m, 1H); 3.41 (d, J=7.1 Hz, 2H); 2.80 (dd, J=15.9, 6.4 Hz, 1H); 2.65 (dd, J=15.9, 8.6 Hz, 1H).

$^{13}$C-NMR: (75 MHz, $C_2D_3N$):

δ (ppm)=197.46 (C=O); 173.24 (C=O); 144.73 ($C_q$); 137.98 ($C_q$); 134.02-127.52 ($C_{Ar}$); 57.29 (CH); 45.11 ($CH_2$); 40.74 ($CH_2$); 38.49 (CH).

Example 1c

Production of the Methoxy-Substituted Compounds

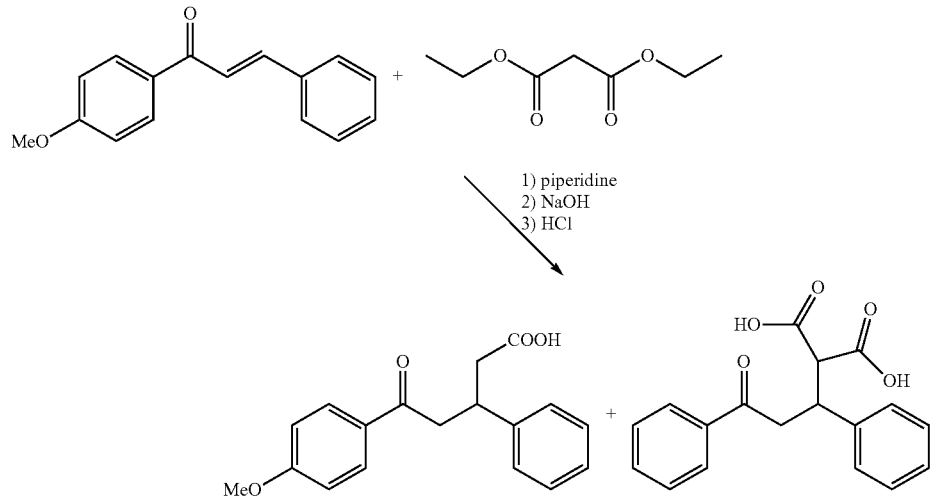

A solution of methoxychalcone, dimethyl malonate, and pyridine was heated in ethanol in a 100 ml round bottom flask with a reflux cooler, and stirred under reflux for 2 days.

After the reaction mixture had cooled, cold 4M caustic soda was dripped in, and the mixture was heated and stirred for 6 hours under reflux. The mixture was then cooled, cold concentrated hydrochloric acid was dripped in at room temperature to pH 1, and the reaction mixture was extracted three times with diethyl ether. The combined organic phases were washed with saturated NaCl solution, then dried over MgSO$_4$; the solvent was removed under vacuum.

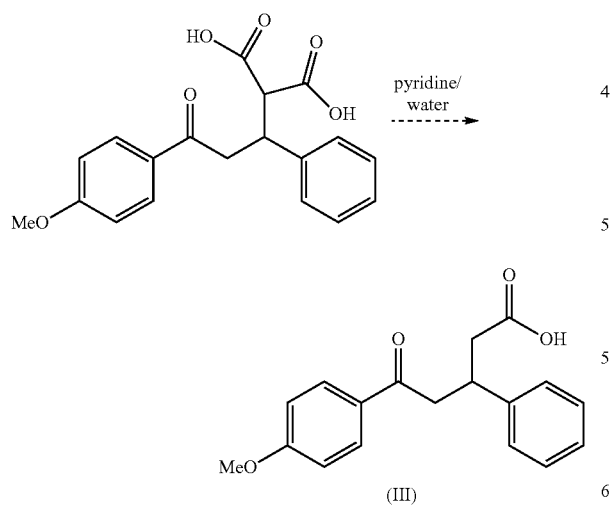

(III)

Because this reaction predominantly yields the dicarboxylic acid, the product was heated under reflux for 2 days in a pyridine/water mixture (4:3). After processing, a $^1$H-NMR spectrum was acquired, in which the characteristic signals for the desired product are identifiable.

$^1$H-NMR: (300 MHz, C$_2$D$_3$N)
δ (ppm)=7.95-7.90 (m, 10H); 3.80 (s, 3H); 3.50 (m, 1H); 3.43-3.41 (d, 2H); 2.75 (dd, 1H); 2.60 (dd, J=15.9, 8.6 Hz, 1H).

Example 1d

Esterification Reaction Yielding methyl-5-oxo-3,5-diphenylpentanoate (AB-02)

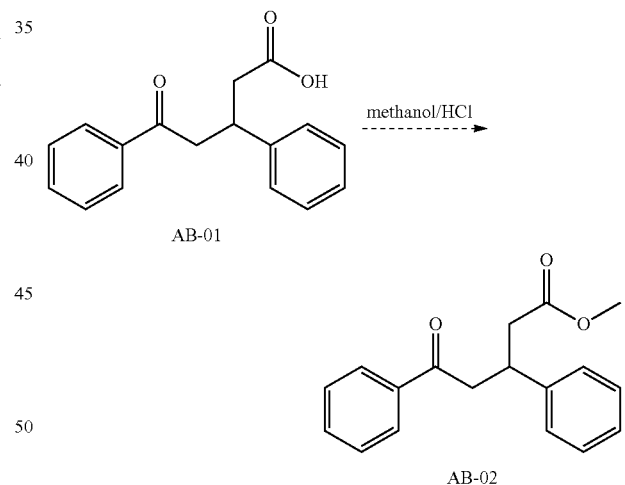

A solution of the carboxylic acid in 7 ml alcohol was prepared in a 50 ml round bottom flask with a reflux cooler. Into this, 0.1 ml HCl was dripped, and heating was performed for 6 hours under reflux.

After the reaction mixture had cooled, 10 ml ice water was added and the reaction mixture was extracted three times with ethyl acetate. The combined organic phases were washed with saturated Na$_2$CO$_3$ solution and with water, then dried over MgSO$_4$ and solvent was removed.

M=282.33 g/mol
GC/MS: (50-300M), m/z: 282, 251, 209, 131, 105, 77, 51.
$t_R$ (50-300M)=10.751 min.
$^1$H-NMR: (300 MHz, C$_2$D$_3$N)

δ (ppm)=7.94-7.18 (m, 10H); 3.79-3.72 (m, 1H); 3.52 (d, J=7.1 Hz, 2H); 3.41-2.65 (dd, 2H).

$^{13}$C-NMR: (75 MHz, C$_2$D$_3$N):

δ (ppm)=199.5 (C=O); 173.1 (C=O); 144.7 (C$_q$); 138.00 (C$_q$); 134.0-124.5 (six signals, C$_{Ar}$); 51.9 (CH$_3$); 45.0 (CH$_2$); 41.3 (CH$_2$); 38.6 (CH).

Example 1e

Ethyl-5-oxo-3,5-diphenylpentanoate (AB-03)

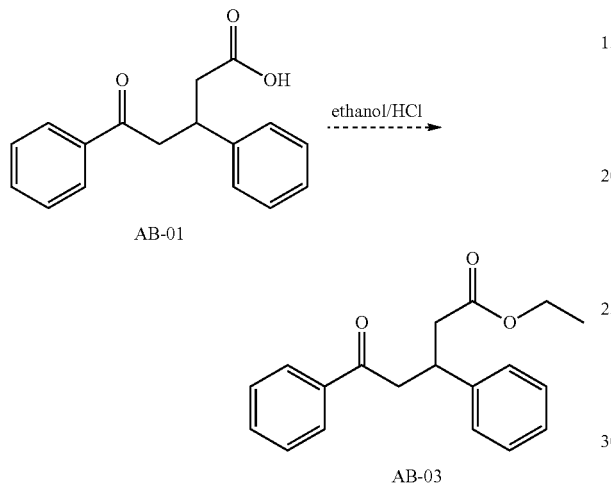

M=296.36 g/mol
GC/MS: (50-300M), m/z: 296, 251, 109, 131, 105, 91, 77, 51.
t$_R$ (50-300M)=10.968 min
$^1$H-NMR: (300 MHz, C$_2$D$_3$N)
δ (ppm)=8.01-7.11 (m, 10H); 4.04-3.93 (q, J=7.1 Hz, 2H); 3.85-3.71 (m, 1H); 3.39 (d, J=7.1 Hz, 2H); 2.77-2.61 (dd, 2H); 1.09 (t, J=7.1 Hz, 3H).

$^{13}$C-NMR: (75 MHz, C$_2$D$_3$N):
δ (ppm)=199.4 (C=O); 172.6 (C=O); 144.69 (C$_q$); 138.0 (C$_q$); 134.0 (C$_{Ar}$); 127.5 (six signals, C$_{Ar}$); 61.0 (CH$_2$); 45.1 (CH$_2$); 41.6 (CH$_2$); 38.7 (CH); 14.4 (CH$_3$).

Example 2

Light Exposure Experiments

Example 2a

Light Exposure Reactions of
5-oxo-3,5-diphenylpentanoic acid (AB-01)

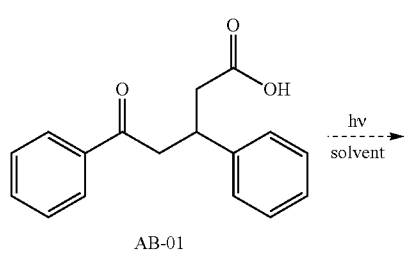

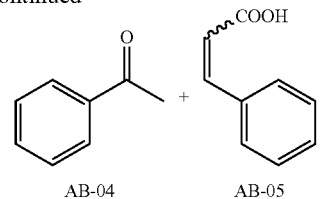

After AAV3, 5.40 mg 5-oxo-3,5-diphenylpentanoic acid was dissolved respectively in 2 ml methanol, acetone, and acetonitrile. Light exposure was applied at the wavelengths λ=350 nm and 300 nm for 5 days. The release products AB-04 and AB-05 were obtained.

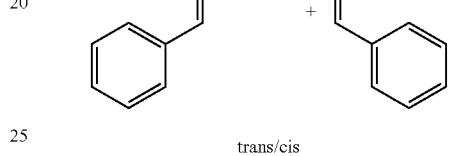

trans/cis $^1$H-NMR: (300 MHz, C$_2$D$_3$N):
δ (ppm)=7.60-7.57 (m, 2H); 7.45-7.40 (m, 3H);
trans: 7.80 (d, 1H); 6.54-6.50 (d, 1H); cis: 6.99 (d, 1H); 5.96 (d, 1H).

Example 2b

Light Exposure Reactions of
methyl-5-oxo-3,5-diphenylpentanoate (AB-02)

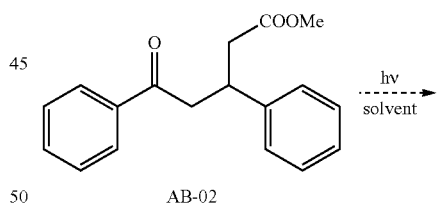

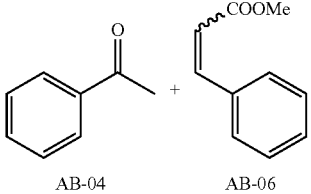

5.64 mg 5-oxo-3,5-diphenylpentanoic acid was dissolved respectively in 2 ml methanol, acetone, and acetonitrile and exposed to light at the wavelengths 2=350 nm and 300 nm for 5 days. The release products AB-04 and AB-06 were obtained.

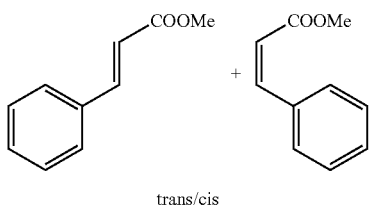 [SMILES: COC(=O)/C=C/c1ccccc1 ; COC(=O)/C=C\c1ccccc1]

trans/cis

¹H-NMR: (300 MHz, CDCl₃)

δ (ppm)=7.50 (m, 2H); 7.25 (m, 3H); 3.50 (s, 3H);

trans: 7.90 (d, 114); 6.50 (d, 1H); cis: 7.00 (d, 1H); 6.00 (d, 1H).

Example 2c

Light Exposure of ethyl-5-oxo-3,5-diphenylpentanoate (AB-02)

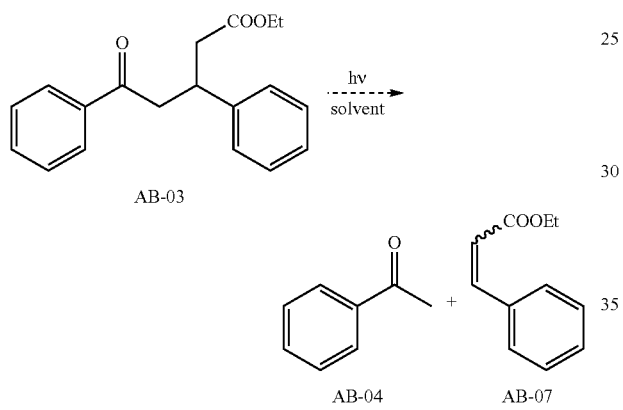

5.72 mg 5-oxo-3,5-diphenylpentanoic acid was dissolved respectively in 2 ml methanol, acetone, and acetonitrile. Light exposure was performed at the wavelengths λ=350 nm and 300 nm for 5 days. The release products AB-04 and AB-07 were obtained.

The compounds produced in this manner exhibited a very good scenting effect when used for textile treatment in washing agents and fabric softeners. In particular, better longevity of the scent impression was observed on the laundry washed therewith and then dried, as compared with washing agents and fabric softeners that contained an equimolar quantity of the corresponding cinnamic acid esters but were otherwise identically configured. The fresh scent impression of the textiles persisted for appreciably longer, both after line drying and in particular after drying in an automatic dryer.

UV-Vis Absorption Spectra of 5-Oxo-3,5-diphenylpentanoic Acid Substituted on the Chromophore, as Compared with Unsubstituted.

The UV-Vis spectra were acquired using a Perkin Elmer Lambda 35 UV/Vis spectrometer. For this, the samples were dissolved in methanol (c=0.1 mM) and measured in quartz cuvettes having a layer thickness of 1 cm. The measured wavelength region was 240 to 440 nm $\lambda_{max}$ is the absorption maximum of the most intense band of the respective spectrum

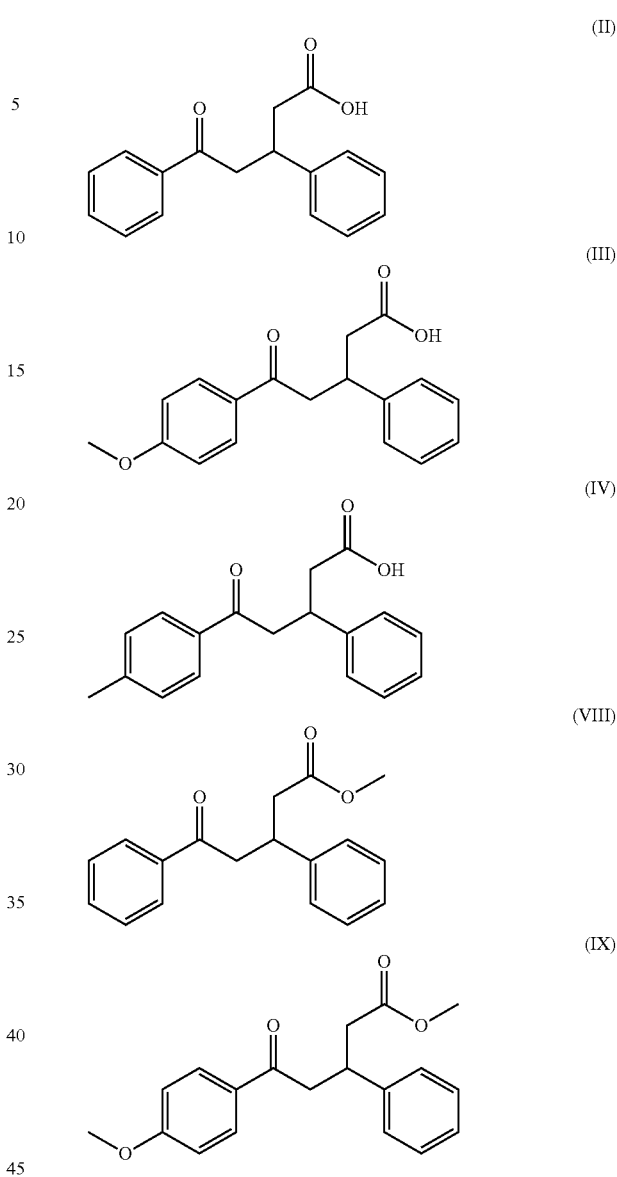

The $\lambda_{max}$ values are:

$\lambda_{max}$(II)=242 nm $\lambda_{max}$(III)=273 nm $\lambda_{max}$(IV)=254 nm $\lambda_{max}$(VIII)=243 nm $\lambda_{max}$(IX)=275 nm While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A compound of the general formula (I)

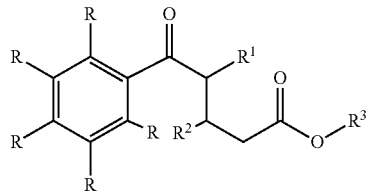

formula (I)

wherein
R1 denotes hydrogen, a linear or branched, substituted or unsubstituted alkyl, aryl, or alkenyl group,
R2 denotes an unsubstituted aryl group, and R3 denotes hydrogen, a linear or branched, substituted or unsubstituted alkyl, aryl, or alkenyl group, and
each R mutually independently denotes hydrogen, an amino group, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl group, acyl group, aryl group, —OH, -NH$_2$, halogen, NH-alkyl, or —N(alkyl)$_2$.

2. The compound according to claim 1, wherein the substituent R1 denotes a linear or branched, substituted or unsubstituted alkyl group having 1 to 6 carbon atoms.

3. The compound according to claim 1, wherein the substituent R3 is hydrogen, a methyl, ethyl, n-pentyl, sec-pentyl, cinnamyl, or citronellyl group.

4. The compound according to claim 1, wherein the substituents R each mutually independently denote hydrogen or methyl or methoxy groups.

5. The compound according to claim 1, corresponding to one of the following formulas (II) to (ILIV)

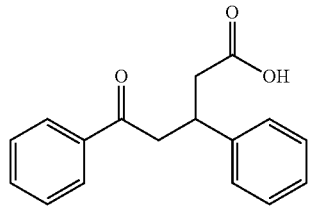

(II)

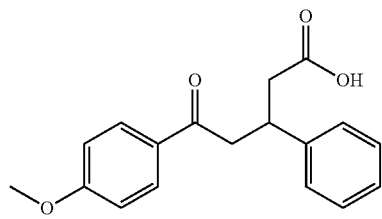

(III)

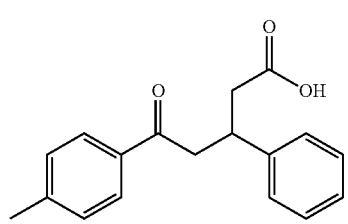

(IV)

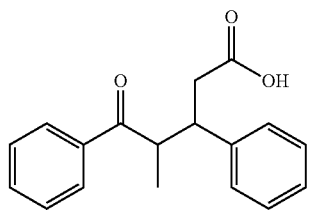

(V)

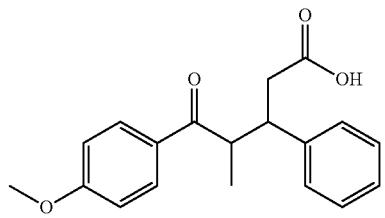

(VI)

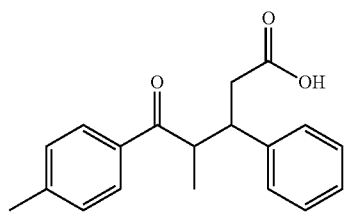

(VII)

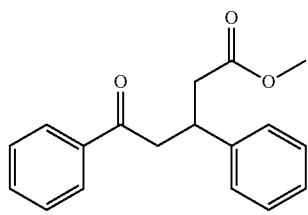

(VIII)

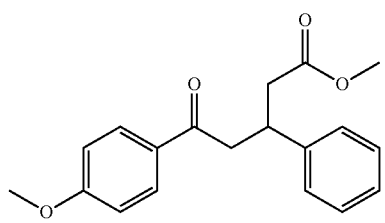

(IX)

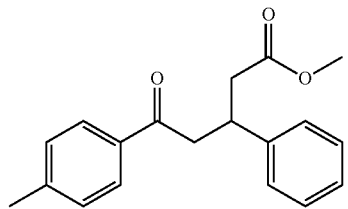

(X)

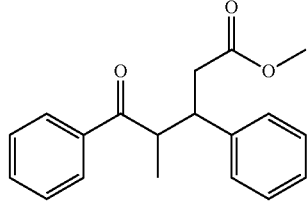

(XI)

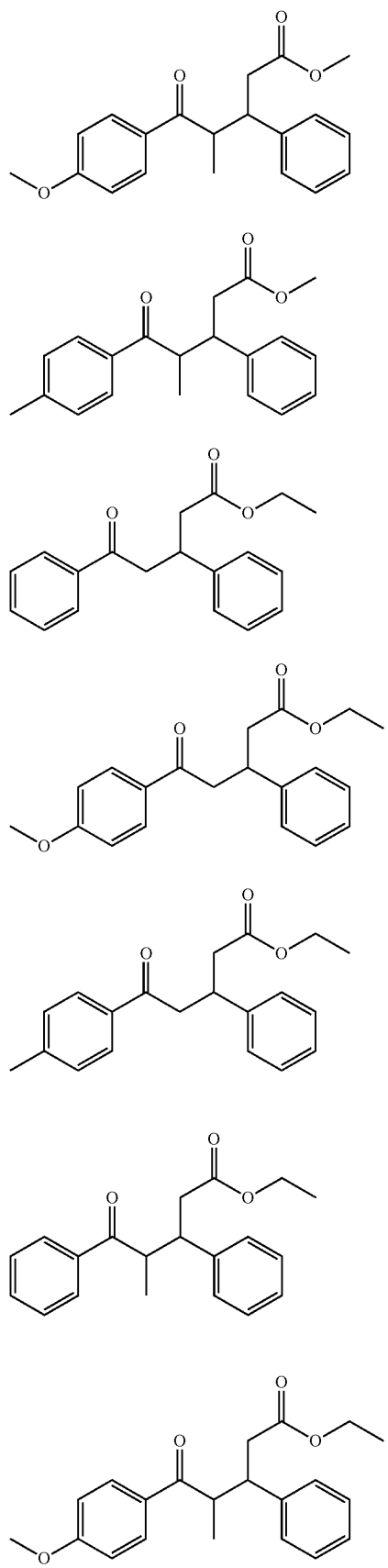
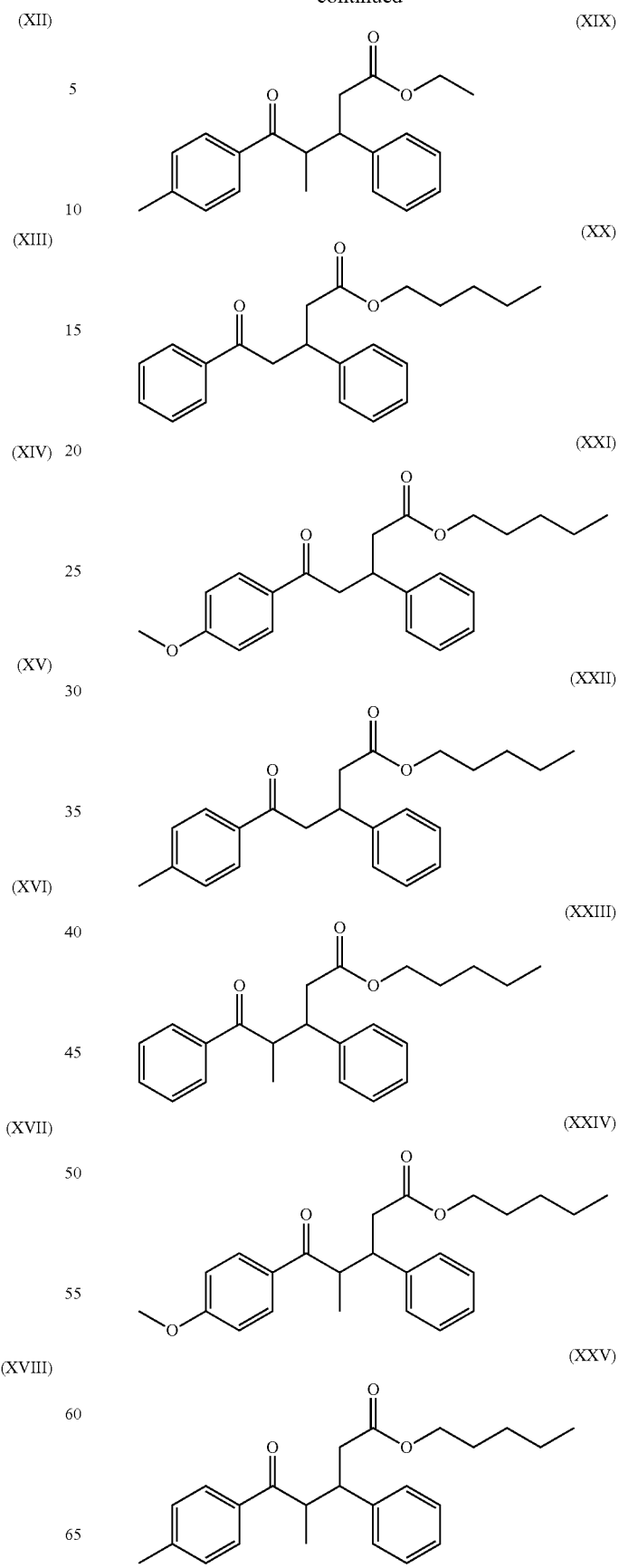

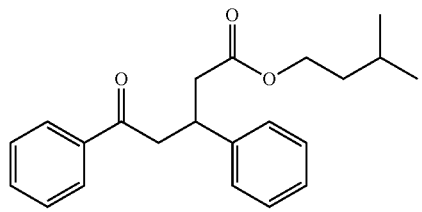
(XXVI)
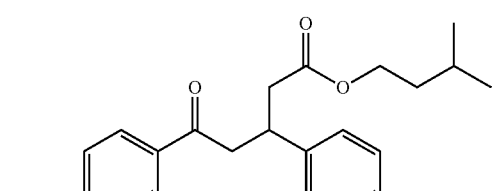
(XXVII)
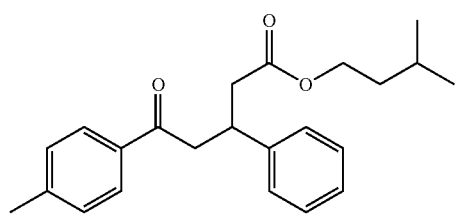
(XXVIII)
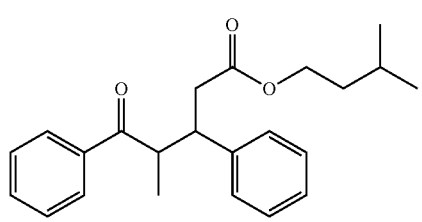
(XXIX)
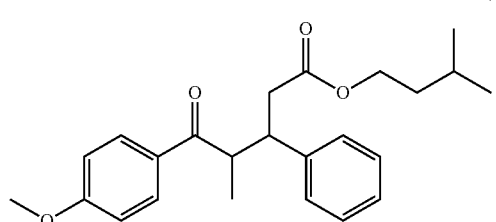
(XXX)
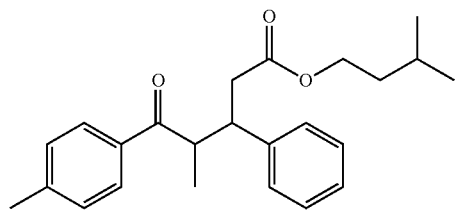
(XXXI)
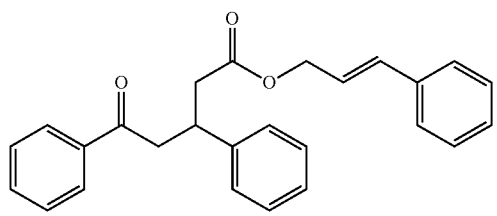
(XXXII)
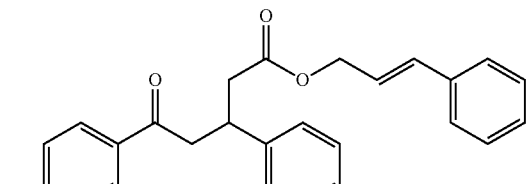
(XXXIII)
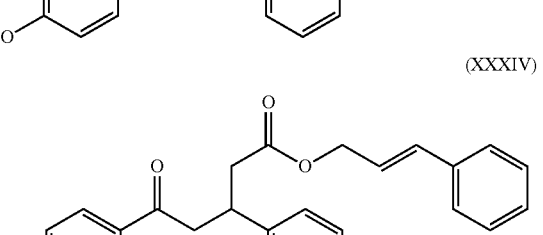
(XXXIV)
(XXXV)
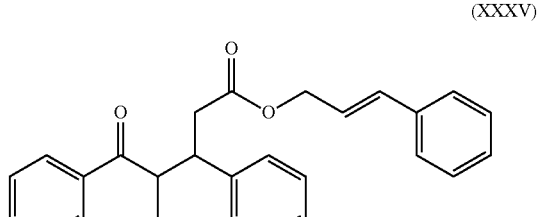
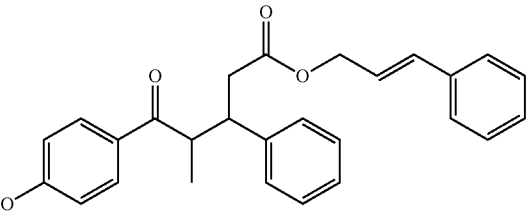
(XXXVI)
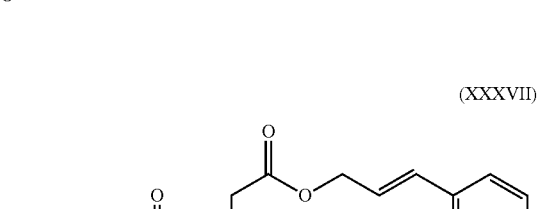
(XXXVII)
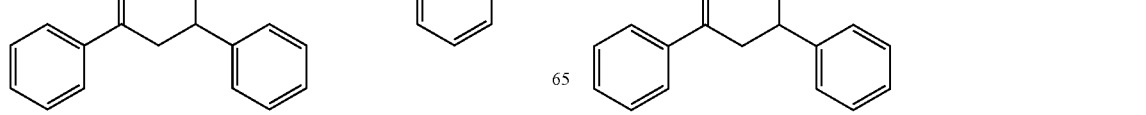
(XXXVIII)

(XXXIX)
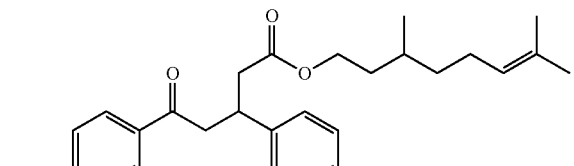

(IL)
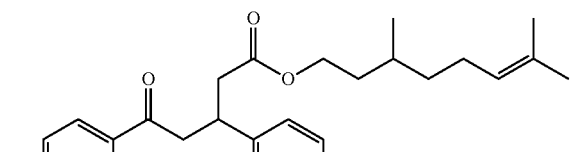

(ILI)
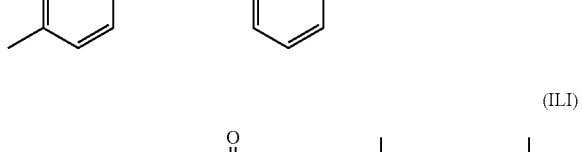

(ILII)
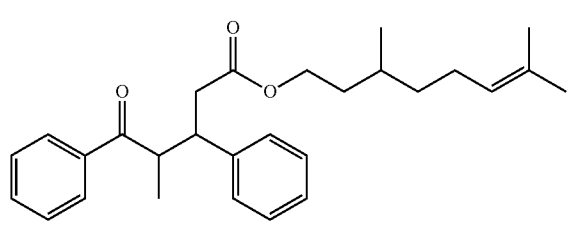

(ILIII)
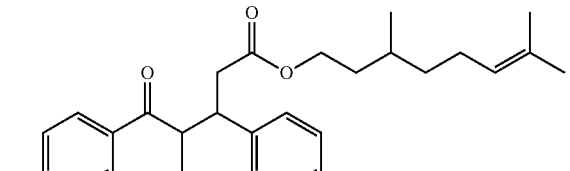

(ILIV)
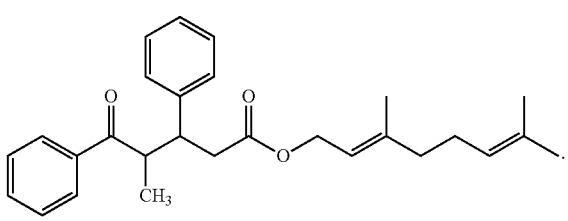

6. A washing or cleaning agent comprising at least one compound according to claim 1.

7. The washing or cleaning agent according to claim 6, wherein said compound comprises between 0.0001 and 5 wt % based on the total agent.

8. The washing or cleaning agent according to claim 7, wherein it contains at least one surfactant selected from the group consisting of anionic, cationic, nonionic, zwitterionic, amphoteric surfactants, and mixtures thereof.

9. A room scenting agent containing at least one compound according claim 1, wherein said compound comprises between 0.0001 and 50 wt %, based on the total agent.

10. A cosmetic agent containing at least one compound according to claim 1, wherein said compound comprises between 0.0001 and 50 wt %, based on the total agent.

11. A method for long-lasting scenting of surfaces, wherein a compound ng to claim 1 is applied onto the surface to be scented, and said surface is then exposed to an electromagnetic radiation comprising the wavelengths from 200 to 400 nm.

* * * * *